US007345755B2

(12) United States Patent
Ogawa et al.

(10) Patent No.: US 7,345,755 B2
(45) Date of Patent: Mar. 18, 2008

(54) DEFECT INSPECTING APPARATUS AND DEFECT INSPECTION METHOD

(75) Inventors: Riki Ogawa, Kawasaki (JP); Toru Tojo, Naka-gun (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 314 days.

(21) Appl. No.: 11/248,124

(22) Filed: Oct. 13, 2005

(65) Prior Publication Data

US 2006/0087649 A1 Apr. 27, 2006

(30) Foreign Application Priority Data

Oct. 14, 2004 (JP) ............................ 2004-300265

(51) Int. Cl.
*G01N 21/00* (2006.01)

(52) U.S. Cl. .................................................. 356/237.5

(58) Field of Classification Search ... 356/237.1–237.6
See application file for complete search history.

(56) References Cited

U.S. PATENT DOCUMENTS 6,654,110 B2 * 11/2003 Yonezawa et al. ....... 356/237.2
2004/0252296 A1 12/2004 Tojo et al.
2005/0002020 A1 1/2005 Inoue et al.
2006/0082782 A1 4/2006 Ogawa et al.

FOREIGN PATENT DOCUMENTS

JP 10-177246 6/1998

OTHER PUBLICATIONS

Ogawa et al., "Defect Inspecting Apparatus", U.S. Appl. No. 11/249,359, filed Oct. 14, 2005.

* cited by examiner

*Primary Examiner*—Tarifur Chowdhury
*Assistant Examiner*—Tara S Pajoohi
(74) *Attorney, Agent, or Firm*—Finnegan, Henderson, Farabow, Garrett & Dunner, L.L.P.

(57) ABSTRACT

In a defect inspecting apparatus, an illumination optical system illuminate a mask having a patterned surface, the optical beam passing through the mask is split into two beam components which is guided in first and second image pickup sensors. The pickup sensors has first and second pickup fields on the patterned surface, which pick up first and second parts of the mask image. The first and second pickup fields are parallel to each other and displaced from each other by (2n+1)xd/2 in the longitudinal direction thereof, where d denotes a longitudinal dimension of each pixel image in the first and second pick up fields and n denotes an integer equal to or larger than 0. The first and second parts of the mask image are merged to form a pattern image, and a defect in the mask is detected on the basis of the pattern image.

24 Claims, 6 Drawing Sheets

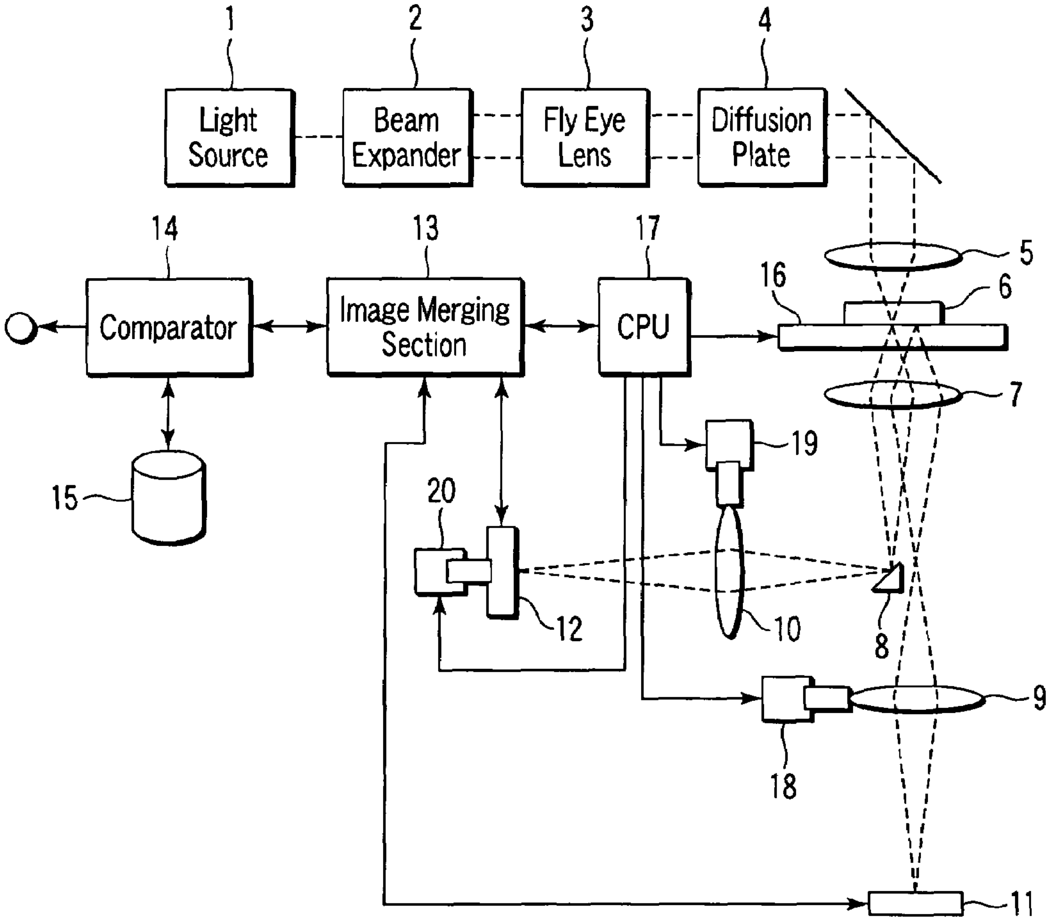
F I G. 1

| | CA1 | CA2 | CA3 | CA4 |
|---|---|---|---|---|
| RA1 | 75 | 100 | 100 | 100 |
| RA2 | 50 | 50 | 100 | 100 |
| RA3 | 50 | 0 | 50 | 100 |
| RA4 | 50 | 0 | 0 | 50 |
| RA5 | 100 | 100 | 100 | 100 |
| RA6 | 100 | 100 | 100 | 100 |

| | CB1 | CB2 | CB3 | CB4 |
|---|---|---|---|---|
| RB1 | 100 | 100 | 100 | 100 |
| RB2 | 100 | 100 | 100 | 100 |
| RB3 | 50 | 100 | 100 | 100 |
| RB4 | 0 | 50 | 100 | 100 |
| RB5 | 0 | 0 | 50 | 100 |
| RB6 | 50 | 50 | 50 | 75 |

| | | C1-1 | C1-2 | C2-1 | C2-2 | C3-1 | C3-2 | C4-1 | C4-2 |
|---|---|---|---|---|---|---|---|---|---|
| R1-1 | 87.5 | 87.5 | 100 | 100 | 100 | 100 | 100 | 100 | 100 |
| R1-2 | 87.5 | 62.5 | 75 | 100 | 100 | 100 | 100 | 100 | 100 |
| R2-1 | 75 | 50 | 50 | 75 | 100 | 100 | 100 | 100 | 100 |
| R2-2 | 75 | 25 | 25 | 50 | 75 | 100 | 100 | 100 | 100 |
| R3-1 | 75 | 25 | 0 | 25 | 50 | 75 | 100 | 100 | 100 |
| R3-2 | 75 | 25 | 0 | 0 | 25 | 50 | 75 | 100 | 100 |
| R4-1 | 75 | 25 | 0 | 0 | 0 | 25 | 50 | 75 | 100 |
| R4-2 | 75 | 50 | 25 | 25 | 25 | 25 | 50 | 62.5 | 87.5 |
| | | 75 | 75 | 75 | 75 | 75 | 75 | 87.5 | 87.5 |

FIG. 6

|  | CB1 | | CB2 | | CB3 | | CB4 | |
|---|---|---|---|---|---|---|---|---|
|  | C1-1 | C1-2 | C2-1 | C2-2 | C3-1 | C3-2 | C4-1 | C4-2 |
| RA1 R1-1 | 87.5 | 100 | 100 | 100 | 100 | 100 | 100 | |
| R1-2 | 62.5 | 75 | 100 | 100 | 100 | 100 | 100 | |
| RA2 R2-1 | 50 | 50 | 75 | 100 | 100 | 100 | 100 | |
| R2-2 | 25 | 25 | 50 | 75 | 100 | 100 | 100 | |
| RA3 R3-1 | 25 | 0 | 25 | 50 | 75 | 100 | 100 | |
| R3-2 | 25 | 0 | 50 | 25 | 50 | 75 | 100 | |
| RA4 R4-1 | 25 | 0 | 0 | 0 | 25 | 50 | 75 | |
| R4-2 | 50 | 25 | 25 | 25 | 25 | 50 | 62.5 | |
| RA5 R5-1 | 75 | 75 | 75 | 75 | 75 | 75 | 87.5 | |

DEFECT INSPECTING APPARATUS AND DEFECT INSPECTION METHOD

CROSS-REFERENCE TO RELATED APPLICATIONS

This application is based upon and claims the benefit of priority from prior Japanese Patent Application No. 2004-300265, filed Oct. 14, 2004, the entire contents of which are incorporated herein by reference.

BACKGROUND OF THE INVENTION

1. Field of the Invention

The present invention relates to a defect inspecting apparatus and a defect inspecting method, and in particular, to defect inspecting apparatus and method that inspect defects on a mask pattern, the mask pattern being formed on a mask such as a reticle.

2. Description of the Related Art

With an increase in the degree of integration of semiconductor devices such as LSIs, efforts are being made to reduce the sizes of mask patterns formed on masks such as reticles. This requires a high performance to be exhibited by defect inspecting apparatuses that inspect mask patterns for defects. Jpn. Pat. Appln. KOKAI Publication No. 10-177246 proposes a defect inspecting apparatus that detects defects by using an image pickup sensor such as a CCD to pickup an image of a mask pattern and comparing the picked-up image with a reference image.

Possible methods for improving the resolution of the defect inspecting apparatus include those for increasing the magnification of a detection optical system and those for increasing the number of pixels in the image pickup sensor. An increase in the magnification of the detection optical system reduces the area of a field region on a surface of the mask on which the pattern is formed. This increases the number of images picked up by the device, necessarily reducing the throughput of defect inspections. On the other hand, an increase in the number of pixels in the image pickup sensor enlarges an illumination field illuminated by an illumination optical system. This hinders the efficient use of illumination light rays. This problem is particularly serious if an image pickup sensor such as a TDI (Time Delay Integration) operation type is used which has a vertically long shape. For example, it is assumed that an increase in the number of pixels has doubled the vertical size of the image pickup sensor. Then, since the illumination optical system normally illuminates a circular illumination field, the area of the illumination field must be quadrupled. This necessarily increases the intensity of an optical beam from the illumination optical system that illuminates the regions of the image pickup sensor except the field region. As a result, the illumination optical beam may become wasteful; the effective use of the illumination optical beam is hindered.

It is important to increase the resolution of the defect inspecting apparatus in order to improve its performance. However, as described above, the improvement of the resolution involves problems such as a decrease in throughput and an impediment to the effective use of the illumination optical beam. Therefore, it is not easy to improve the resolution of the defect inspecting apparatus.

BRIEF SUMMARY OF THE INVENTION

It is an object of the present invention to provide a defect inspecting apparatus which inspects a mask pattern for defects and which can improve resolution.

According to an aspect of the present invention, there is provided a defect inspecting apparatus comprising:

an illumination optical system configured to illuminate a mask having a patterned surface with an illumination optical beam;

an optical splitter configured to split the optical beam passing through the mask into two beam components, which is substantially arranged in an imaging plane on which the optical beam passing through the mask forms an image of the mask;

first and second image pickup sensors each having an array of pixels arranged on a longitudinal direction thereof and first and second pickup fields on the patterned surface, respectively, configured to pick up first and second parts of the mask image in the first and second pickup fields, the first and second pickup fields being parallel to each other and displaced from each other by $(2n+1)\times d/2$ in the longitudinal direction thereof, where d denotes a longitudinal dimension of each pixel image in the first and second pick up fields and n denotes an integer equal to or larger than 0;

image merging part configured to merge the first and second parts of the mask image to form a pattern image, and a defect detector configured to detect a defect in the mask on the basis of the pattern image.

According to another aspect of the present invention, there is provided a defect inspecting apparatus comprising:

an illumination optical system configured to illuminate a mask having a patterned surface with an illumination optical beam;

an optical splitter configured to split the optical beam directed from the mask into two beam components, which is substantially arranged in an imaging plane on which the optical beam passing through the mask forms an image of the mask;

first and second image pickup sensors each having an array of pixels arranged on a longitudinal direction thereof and first and second pickup fields on the patterned surface, respectively, configured to pick up first and second parts of the mask image in the first and second pickup fields, the first and second pickup fields being parallel to each other and displaced from one another by an odd-number multiple of half of a dimension of each pixel image in the first and second pick up fields;

first and second image transfer optical systems configured to transfer the first and second parts of the mask image to the first and second image pickup sensors, respectively;

image merging part configured to merge the first and second parts of the mask image to form a pattern image, and a defect detector configured to detect a defect in the mask on the basis of the pattern image.

According to yet another aspect of the present invention, there is provided a defect inspecting apparatus comprising:

an illumination optical system configured to illuminate a mask having a patterned surface with an illumination optical beam;

first and second optical splitters configured to split the optical beam passing through the mask into three beam components, which is substantially arranged in an imaging plane on which the optical beam passing through the mask forms an image of the mask;

first, second and third image pickup sensors each having an array of pixels arranged on a longitudinal direction thereof and first, second and third pickup fields on the patterned surface, respectively, configured to pick up first, second and third parts of the mask image in the first, second and third pickup fields, the first, second and third pickup fields being parallel to each other, the first and second pickup fields being displaced from each other by (d/3+Nd) in the longitudinal direction thereof, and the second and third pickup fields being displaced from each other by (d/3+Nd) in the longitudinal direction thereof, where d denotes a longitudinal dimension of each pixel image in the first, second and third pick up fields and N denotes an integer equal to or larger than 0;

image merging part configured to merge the first and second parts of the mask image to form a pattern image, and a defect detector configured to detect a defect in the mask on the basis of the pattern image.

According to further aspect of the present invention, there is provided a method of inspecting a defect, comprising:

illuminating a mask having a patterned surface with an illumination optical beam;

splitting the optical beam passing through the mask into two beam components on an imaging plane on which an image of the mask is formed;

picking up first and second parts of the mask image in first and second pickup fields on the patterned surface by utilizing first and second image pickup sensors each having an array of pixels arranged on a longitudinal direction thereof, respectively, the first and second pickup fields being parallel to each other and displaced from each other by (2n+1)×d/2 in the longitudinal direction thereof, where d denotes a longitudinal dimension of each pixel image in the first and second pick up fields and n denotes an integer equal to or larger than 0;

merging the first and second parts of the mask image to form a pattern image, and detecting a defect in the mask on the basis of the pattern image.

According to yet further aspect of the present invention, there is provided a method of inspecting a defect, comprising:

illuminating a mask having a patterned surface with an illumination optical beam;

splitting the optical beam directed from the mask into two beam components on an imaging plane on which an image of the mask is formed;

picking up first and second parts of the mask image in first and second pickup fields on the patterned surface by utilizing first and second image pickup sensors each having an array of pixels arranged on a longitudinal direction thereof, respectively, the first and second pickup fields being parallel to each other and displaced from one another by an odd-number multiple of half of a dimension of each pixel image in the first and second pick up fields;

transferring the first and second parts of the mask image to the first and second image pickup sensors, respectively;

merging the first and second parts of the mask image to form a pattern image, and detecting a defect in the mask on the basis of the pattern image.

According to furthermore aspect of the present invention, there is provided a method of inspecting a defect, comprising:

illuminating a mask having a patterned surface with an illumination optical beam;

splitting the optical beam passing through the mask into three beam components, which is substantially arranged in an imaging plane on which an image of the mask is formed;

picking up first, second and third parts of the mask image in first, second and third pickup fields on the patterned surface by utilizing first, second and third image pickup sensors each having an array of pixels arranged on a longitudinal direction thereof, respectively, the first, second and third pickup fields being parallel to each other, the first and second pickup fields being displaced from each other by (d/3+Nd) in the longitudinal direction thereof, and the second and third pickup fields being displaced from each other by (d/3+Nd) in the longitudinal direction thereof, where d denotes a longitudinal dimension of each pixel image in the first, second and third pick up fields and N denotes an integer equal to or larger than 0;

merging the first and second parts of the mask image to form a pattern image, and detecting a defect in the mask on the basis of the pattern image.

BRIEF DESCRIPTION OF THE SEVERAL VIEWS OF THE DRAWING

FIG. 1 is a block diagram showing an optical system and its peripheral devices in a defect inspecting apparatus in accordance with an embodiment of the present invention;

FIGS. 4A and 4B are plan views schematically showing the distribution of relative luminance in an image acquired by the defect inspecting apparatus shown in FIG. 1;

FIG. 6 is a plan view schematically showing the distribution of the relative luminance in an image obtained by processing the image shown in FIGS. 4A and 4B;

DETAILED DESCRIPTION OF THE INVENTION

Figure 2:
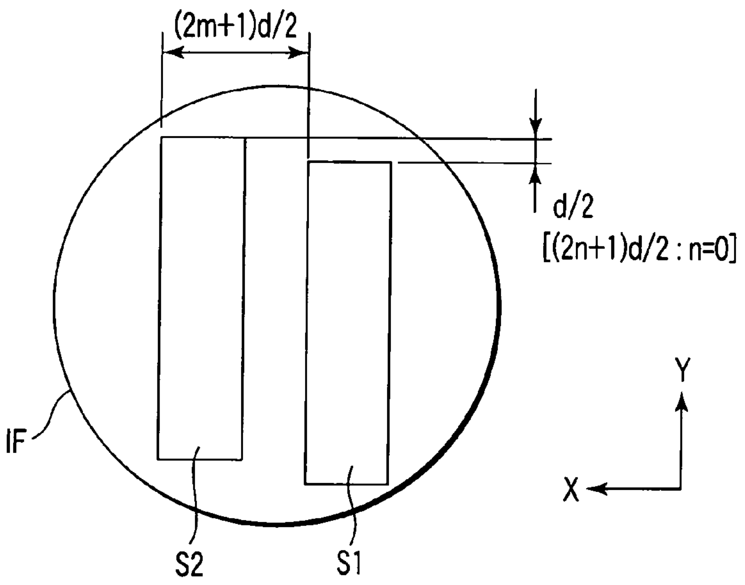
FIG. 2 is a plan view schematically showing the relationship between an illumination field on a mask patterned surface and a pickup field, on the mask patterned surface, of an image pickup sensor in the defect inspecting apparatus shown in FIG. 1.

With reference to the drawings, description will be given of a defect inspecting apparatus that inspects a mask for defects according to an embodiment of the present invention.

FIG. 1 is a block diagram showing a defect inspecting apparatus that inspects a mask for defects according to the embodiment of the present invention.

An illumination optical system illuminates a mask surface on which a predetermined pattern is formed, i.e., a patterned surface on a mask 6 such as a reticle, with an optical beam, for example, a laser beam, emitted from a light source 1 shown in FIG. 1. A Köhler illumination optical system is preferably used as an illumination optical system that uniformly illuminates the mask surface.

In the illumination optical system, the following are arranged on an optical path: a beam expander, i.e., collimator lens 2, which expands or collimates an optical beam from the light source 1, and a fly eye lens, i.e., a compound eye lens 3, in which a large number of segment lenses each having the same lens power are two-dimensionally arranged. Moreover, the following are arranged on the optical path of the optical system: an optical element, for example, a diffusion plate, which suppresses the interference between the components of the optical beam, i.e., the laser beam, for example, a diffusion plate and a condenser lens 5 for converging the optical beam, i.e., the laser beam toward the mask surface.

In the illumination optical system, a collimated optical beam from the light source 1 is incident on the fly eye lens 3 which converges the optical beam to form a plurality of convergence points. The diffusion plate 4 diffuses a plurality of beam components diverged from the plurality of convergence points. The diffused beam components are incident on the condenser lens 5, which then collimates and directs the beam components to the mask surface. The condenser lens 5 is focused on the convergence points of the fly eye lens 3. Accordingly, images of light emitting points of the light source 1 are formed at the respective convergence points. Light rays from the light emitting point images are directed to the surface of the photolithography mask. Consequently, the mask surface is uniformly illuminated with the light rays.

The illumination light rays applied to the mask 6 are transmitted through a transparent part of the mask. The transmitted beam components of the light rays are incident on an objective lens and are directed to an image forming surface on which an image of the mask is formed by an objective lens 7. A beam splitter 8 is placed on the image forming surface. The beam splitter 8 splits the optical beam components emerging from the mask. The beam splitter 8 picks up one of the optical components and directed to an imaging optical system 10, which is incident on an image pickup sensor 12 via the imaging optical system 10. The image pickup sensor 12 then picks up a part of a mask image contained in the optical beam component. The other of the optical beam components not incident on the beam splitter 8 is directed to the imaging optical system 9 and incident on an image pickup sensor 11 via the imaging optical system 9. The image pickup sensor 11 then picks up an image contained in the optical beam components. Each of the image pickup sensors 11 and 12 has an array of pixels and is, for example, of a TDI type having a vertically long shape.

FIG. 2 is a plan view showing an illumination field IF on the patterned surface of the mask 6 which has a field illuminated with light rays and pickup fields S1 and S2 which are photographed by the image pickup sensors 11 and 12. As shown in FIG. 2, the image pickup sensors, i.e., image sensors 11 and 12, are arranged so that both the pickup field S1 of the image pickup sensor 11 and the pickup field S2 of the image pickup sensor 12 are located within the illumination field IF of the illumination optical system and are arranged in parallel. The beam splitter 8 is placed at a position where an image of the mask pattern is formed by the objective lens 7. Accordingly, as shown in FIG. 2, the pickup field S1 of the image pickup sensor 11 can be reliably separated from the pickup field S2 of the image pickup sensor 12.

The size, on the patterned surface of the mask 6, of each of the pixels in the image pickup sensor 11 is equal to that of each of the pixels in the image pickup sensor 12. The size is defined as a pixel dimension d in both Y direction and X direction (perpendicular to a longitudinal direction). Here, the Y direction corresponds to the longitudinal direction of the pickup fields S1 and S2 of the image pickup sensor 11 and 12. The X direction is perpendicular to the longitudinal direction. Each of the pixel arrays of the image pickup sensors 11, 12 is arranged in the Y direction.

The pickup fields S1 and S2 of the image pickup sensor 11 and 12 are parallel to and are displaced from each other in the longitudinal direction. The amount by which the pickup fields S1 and S2 are displaced from each other in the longitudinal direction (Y direction) is set equal to an odd-number multiple of the dimension of a half pixel, i.e., $(2n+1)\times d/2$ (n is an integer equal to or larger than 0). In the example shown in FIG. 2, the displacement amount is defined by d/2 ($(2n+1)\times d/2$: n=0). Further, the amount of displacement between the pickup fields S1 and S2 in the direction (X direction) perpendicular to the longitudinal direction is also set equal to the odd-number multiple of the dimension of the half pixel. However, since the pickup fields S1 and S2 are separated from each other in the X direction, that is, the pickup fields S1 and S2 do not overlap, the displacement amount is defined by $(2m+1)\times d/2$ (m is an integer equal to or larger than 1).

When an image pickup operation is started, a stage 16 on which the mask 6 is placed is moved within a plane (XY plane) orthogonal to the optical beam axis of the optical system. The mask 6 is scanned using the pickup fields S1 and S2. Mask pattern images of the pickup fields S1 and S2 are acquired all over the mask 6. Specifically, the mask 6 is continuously scanned in the X direction (shown in FIG. 2) of the stage 16 from the end to end of an inspected area using the pickup fields S1 and S2. Subsequently, the stage 16 is moved in the Y direction step by step. The mask 6 is thus continuously scanned in the X direction of the stage 16 using the pickup fields S1 and S2. Thus, for the entire inspected area of the mask 6, the continuous movement in the X direction and the step movement in the Y direction are repeated to pick up images of the entire surface of the mask 6 using the pickup fields S5 and S2 of the image pickup sensors 11 and 12. A host computer 17 controls the moving operation of the stage 16, the image pickup operation of the image pickup sensors 11 and 12, and other operations.

The image pickup sensors 11 and 12 pick up first and second images; the first and second images are superimposed on each other by an image merging section 13 that synthesizes the first and second images. Since the pickup fields S1 and S2 of the image pickup sensors 11 and 12 are displaced from each other by the odd-number multiple of the dimension of the half pixel, the first and second images picked up by the image pickup sensors 11 and 12 are also displaced from each other by the odd-number multiple of the dimension of the half pixel. Consequently, the synthesized image obtained in the merging section 13 by merging the first and second images corresponds substantially to an image obtained by photographing the half pixel. This image has a higher resolution than those picked up individually by the image pickup sensors 11 and 12. It is therefore possible to acquire an image of the mask pattern at a high resolution, the mask pattern being formed on the patterned surface of the mask 6.

The high-resolution image provided by the image merging section 13 is sent to a comparing section 14, which then compares the image with a reference image stored in a storage section 15. As a result, the difference between the high-resolution image provided by the image merging section 13 and the reference image is detected as a defect in the mask pattern.

The defect inspecting apparatus shown in FIG. 1 comprises magnification varying mechanisms 18 and 19 that can vary the magnifications of the imaging optical systems 9 and 10. When the magnifications of the imaging optical systems 9 and 10 are changed, the pickup fields S1 and S2, on the patterned surface of the mask 6, of the image pickup sensors 11 and 12 are also changed. Thus, to maintain a relationship such as the one shown in FIG. 2, a position adjusting section is provided which adjust the positional relationship between the image pickup sensors 11 and 12 in accordance with the magnifications of the imaging optical systems 9 and 10. Specifically, the position adjusting section corresponds to a moving mechanism 20 that can move the position of the image pickup sensor 12. The host computer 17 automatically controls the moving mechanism 20 and the magnification varying mechanisms 18 and 19. Accordingly, even when the magnifications of the imaging optical systems 9 and 10 are changed, the pickup fields S1 and S2 of the image pickup sensors 11 and 12 can always maintain a relationship such as the one shown in FIG. 2.

Now, a detailed description will be given of an image acquiring operation of the above defect inspecting apparatus as well as processing of the image acquired.

Figure 3:
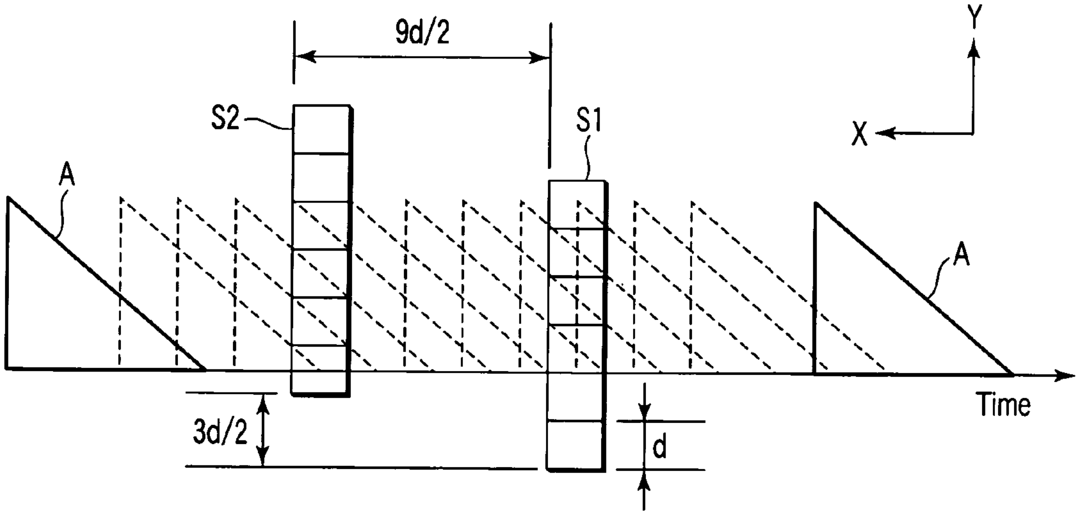
FIG. 3 is a diagram illustrating an image acquiring operation during an inspecting process in the defect inspecting apparatus shown in FIG. 1.

As described above, the two pickup fields S1 and S2 are displaced from each other by the odd-number multiple of the dimension of the half pixel. Accordingly, even though the spacing between the two pickup fields S1 and S2 is arbitrary, two sensor images of the same region can be displaced from each other by the distance corresponding to the half pixel after the entire surface of the mask 6 has been inspected. By way of example, it is assumed that the line sensor fields S1 and S2 with the pixel dimension d are arranged on the surface of the mask 6 in a continuous moving direction of the mask 6 moved using the table 16, as shown in FIG. 3. It is further assumed that a triangular pattern A is formed on the patterned surface of the mask 6 to block light rays and that the triangular pattern A is moved as the mask 6 is moved using the stage 16. Each of the image pickup sensors 11 and 12 is composed of 1×6 pixels. The dashed lines shown in FIG. 3 show the position of the pattern photographed at each point in time when the image pickup sensors 11 and 12 load data. The two image pickup sensors 11 and 12 load data at the same time. The spacing between the sensor fields S1 and S2 is defined as 9d/2 in the continuous moving direction of the mask and as 3d/2 in a direction orthogonal to the continuous moving direction. Output images provided by the sensors are shown in shown in tables and schematic diagrams. The spacing between the two sensors is the odd-number multiple of the dimension of the half pixel. Accordingly, images of the region A provided by the two sensors are displaced from each other by the distance corresponding to the dimension of the half pixel.

FIGS. 4A and 4B schematically show the distribution of intensity, i.e., luminance, in the images picked up by the image pickup sensors 11 and 12. FIG. 4A shows the distribution of pixel intensity in the image composed of pixels sequentially provided by the image pickup sensor 11, having the pickup field S1. FIG. 4B shows the distribution of pixel intensity in the image composed of pixels sequentially provided by the image pickup sensor 12, having the pickup field S2. In FIGS. 4A and 4B, a dotted part corresponds to the shape of the light blocking pattern A shown by the dashed lines. Naturally, in the dotted part, the relative light intensity is lower. In FIGS. 4A and 4B, the pixels are designated by columns CA1 to CA4 and CB1 to CB4 and rows RA1 to RA6 and RB1 to RB6. The relative intensity detected in each pixel is shown as a number in the corresponding pixel designated by the corresponding ones of these rows and columns. As is clear from FIGS. 4A and 4B, outside the light blocking pattern A, the image pickup sensors 11 and 12 detect light rays having a relative intensity 100, because all the light rays are transmitted through the mask. If the light rays are blocked by the light blocking pattern A, almost no light rays reach the image pickup sensor 11 or 12. As a result, light rays with a relative intensity of zero are detected. At the boundary of the light blocking pattern A, light rays constituting a part of the bundle of light rays are blocked by the light blocking pattern A, while the other light rays reach the image pickup sensors 11 and 12. Consequently, an intermediate relative intensity of 50 or 75 is detected which is between the relative intensities 0 and 100. The intermediate relative intensity is determined by the percentage of each image taken up by the image part of the light blocking pattern A.

Figure 5:
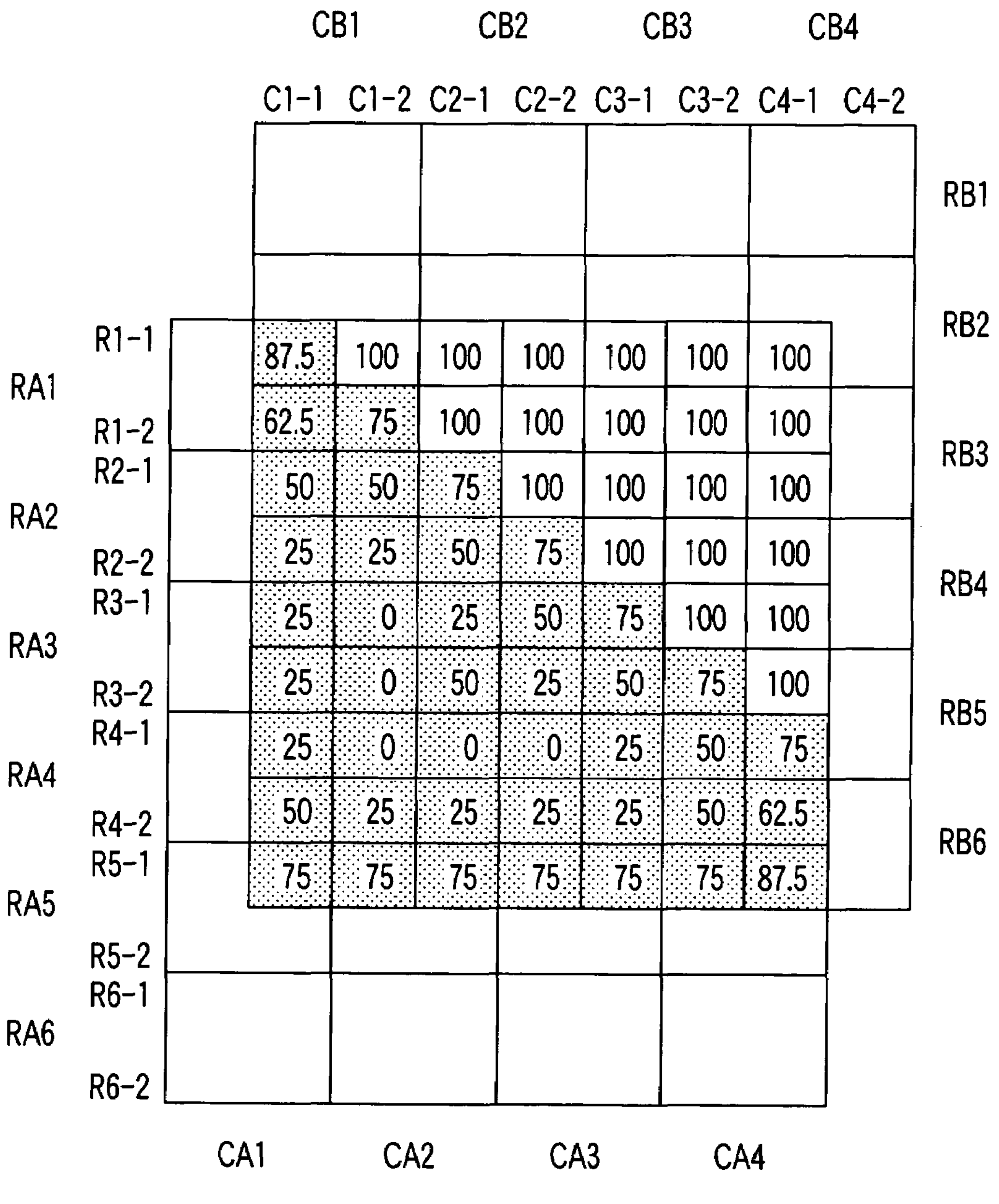
FIG. 5 is a plan view schematically showing the distribution of the relative luminance in an image obtained by processing the image shown in FIGS. 4A and 4B.

FIG. 5 shows the distribution of the pixel density in the image obtained by synthesizing the images picked up by the image pickup sensors 11 and 12. For the rows, the image shown in FIG. 4A and picked up by the image pickup sensor 11 is displaced from the image shown in FIG. 4B and picked up by the image pickup sensor 12, by the distance corresponding to the dimension of the half pixel, in both X and Y directions. For the columns, the images are displaced from each other by the distance corresponding to the dimension of 1.5 pixels in both directions. Accordingly, when the image picked up by the image pickup sensor 11 is superimposed on the image picked up by the image pickup sensor 12, the substantial number of pixels is quadrupled. This results in a high-resolution image. The intensity of each pixel in the high-resolution image is set equal to the average value of the intensity of each pixel in the image picked up by the image pickup sensor 11 and the intensity of each pixel in the image picked up by the image pickup sensor 12.

As described above, the image shown in FIG. 5 and obtained by the superimposition is expressed by a resolution double that of each of the original images shown in FIGS. 4A and 4B. In other words, to provide a high-resolution display, each pixel in the original images shown in FIGS. 4A and 4B offers information for a 2×2 region in the high-resolution image. The two original images shown in FIGS. 4A and 4B are superimposed on each other so as to be displaced from each other by the distance corresponding to the dimension of the half pixel. The images are then averaged. This process enables the original images shown in FIGS. 4A and 4B to be converted into an image having a double resolution as shown in FIG. 5.

In the example shown in FIG. 5, a combination of the pixel (CA1, RA1) and the pixel (CB1, RB2) allows the determination of the relative luminance of the quarter pixel (C1-1, R1-1). That is, the relative luminance (75) of the pixel (CA1, RA1) is added to the relative luminance (100) of the pixel (CB1, RB2) to determine the relative luminance (87.5) of the quarter pixel (C1-1, R1-1). Likewise, the relative luminance (75) of the pixel (CA1, RA1) is added to the relative luminance (50) of the pixel (CB1, RB3) to determine the relative luminance (62.5) of the quarter pixel (C1-1, R1-2). Further, the relative luminance (100) of the pixel (CA2, RA1) is added to the relative luminance (50) of the pixel (CB1, RB3) to determine the relative luminance (75) of the quarter pixel (C1-2, R1-2). Such processing is repeated to determine the relative luminances of all the quarter pixels defined by the columns C1-1 to C4-1 and the rows R1-1 to R5-1 as shown in FIG. 5. That is, the distribution of the pixel intensity on the mask pattern is obtained, which shows the intensity of each quarter pixel. The pixel intensity distribution shown in FIG. 5 exhibits a fourfold higher resolution than the pixel intensity distributions shown in FIGS. 4A and 4B by a factor of 4. Consequently, the accuracy of inspection of the mask pattern can be substantially improved.

Figure 7:
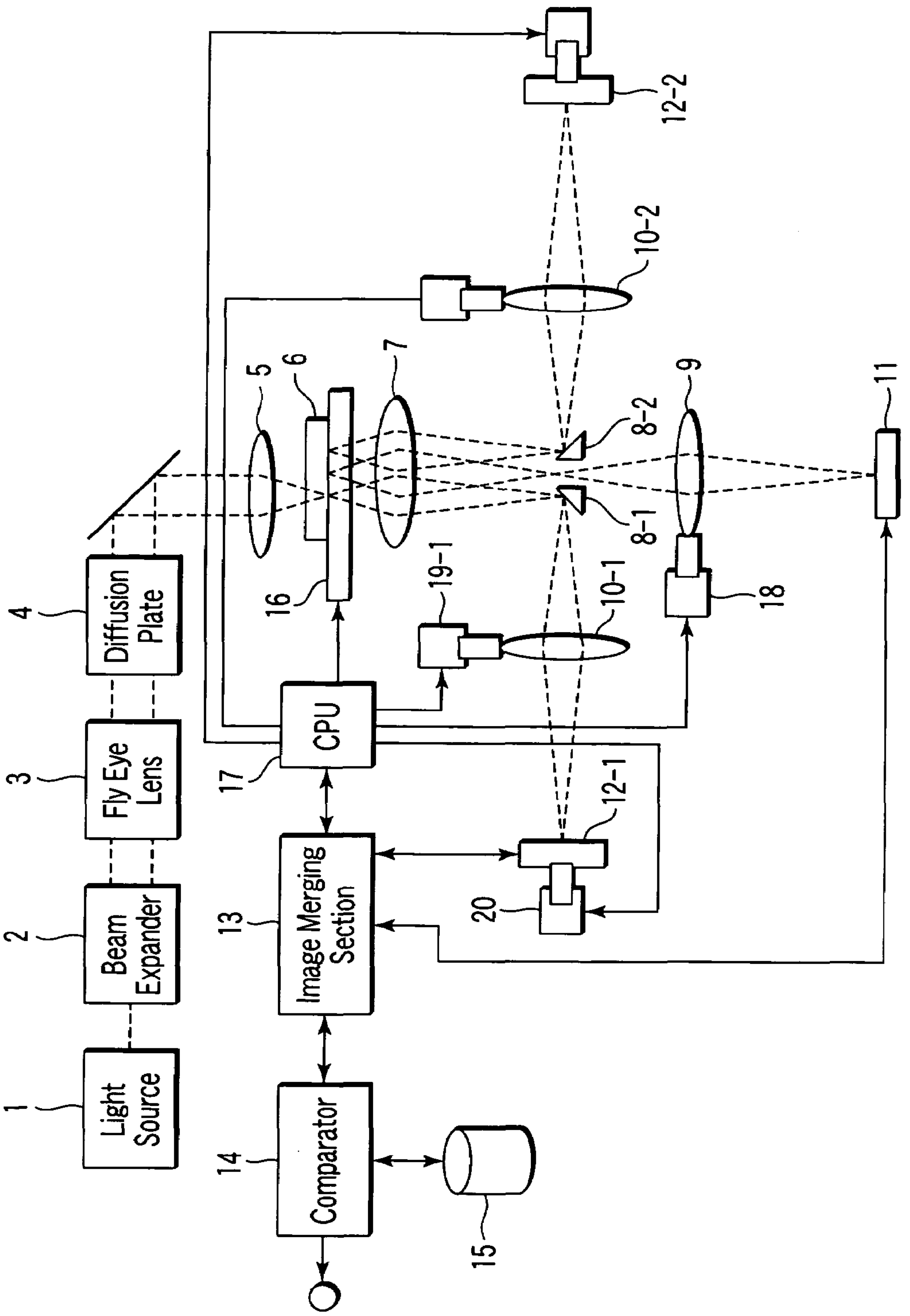
FIG. 7 is a block diagram showing an optical system and its peripheral devices in a defect inspecting apparatus in accordance with another embodiment of the present invention.
Figure 8:
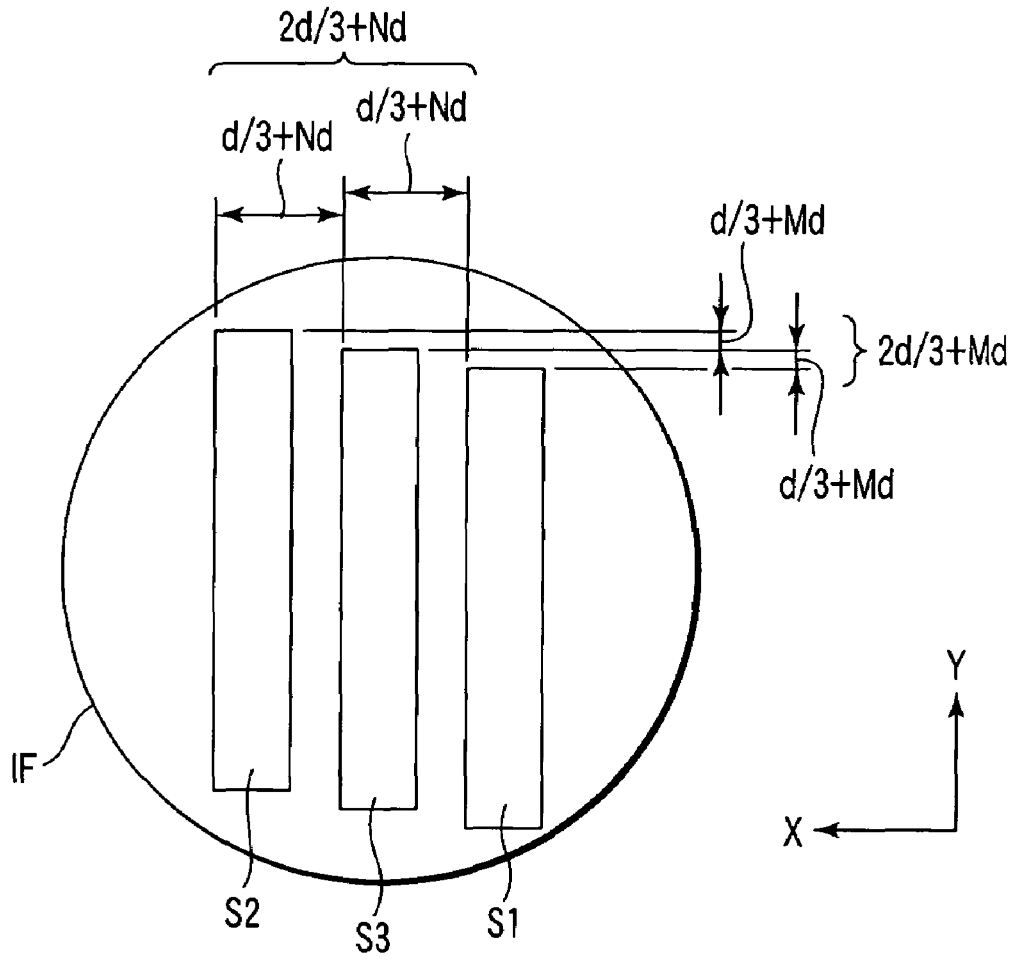
FIG. 8 is a plan view schematically showing the relationship between an illumination field on a mask patterned surface and a pickup field, on the mask patterned surface, of an image pickup sensor in the defect inspecting apparatus shown in FIG. 6.

Obviously, by further increasing the number of pixels acquired by the image pickup sensors 11 and 12, it is possible to obtain a high-resolution pixel intensity distribution for 9×9 quarter pixels as shown in FIG. 7 or for more quarter pixels.

In the above description, the light intensities of pixels are added together and averaged to acquire a pixel intensity distribution for quarter pixels. However, it is sufficient to compare a comparison target pattern with a pixel intensity distribution acquired rather than displaying the actual image. Thus, obviously, a reference distribution may be compared with the distribution of differences between the light intensities of the pixels and a reference value or a distribution acquired by another arithmetic process.

In the above inspecting apparatus, the bundles of light rays, i.e., the light beam, directed to the two detection optical systems are separated from each other on the mask image formed surface. This enables the spacing between the pickup fields to be set at an arbitrary value. As shown in FIG. 2, if line sensors or TDI sensors are used, both pickup fields are arranged parallel to each other in the direction orthogonal to the direction in which the pixels are arranged. This enables the illumination field to be effectively used.

The spacing, i.e., distance between the two sensors must be the odd-number multiple of the dimension of the half pixel in the direction orthogonal to the continuous moving direction of the mask. However, in the continuous moving direction, the spacing between the two sensors need not be set equal to the odd-number multiple of the dimension of the half pixel. The spacing between the two sensors can be arbitrarily set by adjusting loading timings for the two sensors.

As described above, in the present embodiment, on the patterned surface of the mask 6, the pickup field S1 of the image pickup sensor 11 is displaced from the pickup field S2 of the image pickup sensor 12 by the odd-number multiple of the dimension of the half pixel. Accordingly, a high-resolution image can be acquired by synthesizing the image picked up by the image pickup sensor 11 and the image picked up by the image pickup sensor 12. Further, the beam splitter 8 is placed at the position where an image of the mask pattern is formed. Consequently, the pickup field S1 of the image pickup sensor 11 can be reliably separated from the pickup field S1 of the image pickup sensor 12. The pickup fields S1 and S2 can be arranged in parallel within the illumination field of the illumination optical system. Therefore, a high-resolution image can be acquired without the need to enlarge the illumination field of the illumination optical system. It is thus possible to effectively utilize the illumination optical beams and to improve the resolution of the defect inspecting apparatus.

In the above embodiment, on the patterned surface of the mask 6, the pickup field S1 of the image pickup sensor 11 is displaced from the pickup field S2 of the image pickup sensor 12 by the odd-number multiple of the dimension of the half pixel, in both Y direction (longitudinal direction of the pickup field) and X direction (perpendicular to the longitudinal direction). However, the pickup fields need not be set as described above in the X direction. That is, in the X direction, the mask is continuously moved in the X direction. Accordingly, by making an image pickup timing for the image pickup sensor 11 different from an image pickup timing for the image pickup sensor 12, it is possible to displace the image pickup region of the image pickup sensor 11 from the image pickup region of the image pickup sensor 12 by the distance corresponding to the dimension of the half pixel.

Further, in the above embodiment, the pixel dimension on the patterned surface of the mask 6 is defined as d in both X and Y directions. However, the pixel dimension (d) in the X direction may be different from that (d') in the Y direction.

The above defect inspecting apparatus utilizes the two image forming systems and the two sensors. However, the defect inspecting apparatus may be adapted to use three image forming systems and three sensors to obtain a triple resolution. Moreover, with spatial conditions permitting, the defect inspecting apparatus may be generally adapted to use N image forming systems and N sensors to obtain an N-fold resolution.

With reference to FIG. 7, description will be given of a variation of a mask defect inspecting apparatus comprising three image forming systems and three sensors. Like the inspecting apparatus shown in FIG. 1, the inspecting apparatus shown in FIG. 7 carries out transmissive inspections in which it utilizes an optical beam transmitted through a sample such as a mask to inspect the mask. However, the detection optical system comprises three image forming systems and three sensors, i.e., image pickup sensors 11, 12-1, and 12-3.

In the inspecting apparatus shown in FIG. 7, the beam expander 2, the fly eye lens 3, a laser coherency reducing mechanism 4, and the condenser lens 5 cooperate in subjecting the mask 6 to uniform KÖhler illumination with a laser optical beam emitted by the light source 1. The optical beam applied to the mask is then transmitted through a transparent part of the mask and is converged by the objective lens 7. Subsequently, at the mask image formed surface, the optical beam is separated into three bundles of optical beams by beam splitters 8-1 and 8-2. Detection optical systems 10-1 and 10-2 form the optical beams reflected by the beam splitters 8-1 and 8-2 into images on image pickup sensors, i.e., sensors 12-1 and 12-2, respectively. The detection optical system 9 forms the optical beam having passed through the beam splitters 8-1 and 8-2, into an image on the image pickup sensor, i.e., the sensor 11.

The merge circuit 13 superimposes the three mask images detected by the sensors on one another to convert them into a high-resolution image, which is then sent to the comparator 14. The comparator compares the picked-up image with a reference image to output the difference between them as a defect in the mask. The reference image is stored in the storage 15 and read as required. The mask is placed on a precision stage 26 and is entirely scanned by the host computer 17.

Then, as shown in FIG. 7, the detection optical systems 9, 10-1, and 10-2 form detection fields S1, S2, and S3 within the common visual field of the objective lens 7. To effectively use the illumination field, the three pickup fields S1, S2, and S3 are separated from one another. In this case, when the pickup field S1 is used as a reference, the second pickup field S2 is displaced from the pickup field S1 by $d/3+Nd$ (d is the pixel dimension and N is an integer) along the X direction. The third pickup field S3 is displaced from the pickup field S1 by $2d/3+Nd$ (d is the pixel dimension and N is the integer) along the X direction. Further, when the pickup field S1 is used as a reference, the second pickup field S2 is displaced from the pickup field S1 by $d/3+Md$ (d is the pixel dimension and M is an integer) along the Y direction. The third pickup field S3 is displaced from the pickup field S1 by $2d/3+Md$ (d is the pixel dimension and M is the integer) along the Y direction.

The pickup fields S1, S2, and S3 are thus set to acquire three images similar to those shown in FIGS. 4A and 4B. The three images are superimposed on one another to acquire an image similar to that shown in FIG. 5. As described above with reference to FIGS. 4A and 5, the superimposed image is expressed at a resolution triple that of the original image. In other words, to provide a high-resolution display, each pixel in the original image offers information for a 3×3 region in the high-resolution image. The three original images are superimposed on one another so as to be displaced from one another by the distance corresponding to the dimension of a one-third pixel. The images are then averaged. This process enables the original images to be converted into an image having a triple resolution.

Even with the apparatus shown in FIG. 6, each of the distances between the three sensors must be an integral multiple of the one-third pixel in the direction orthogonal to the continuous moving direction of the mask. However, in the continuous moving direction, each of the distances between the three sensors need not be set equal to the integral multiple of the one-third pixel. Each of the distances between the three sensors can be arbitrarily set by adjusting the loading timings for the three sensors.

In the above embodiment, the transmissive optical system is described by way of example. However, the above method is applicable to a reflective optical system.

The embodiments of the present invention have been described. However, the present invention is not limited to the above embodiments. Many variations may be made to the embodiments without departing from the spirit of the present invention. The above embodiments include inventions at various levels. Thus, various inventions can be extracted by appropriately combining the disclosed constitution requirements. For example, even if any disclosed constitution requirements are omitted, inventions can be extracted provided that the resulting embodiment exerts predetermined effects.

The present invention can provide a high-resolution image without the need to enlarge the illumination field of the illumination optical system. It is thus possible to effectively utilize the illumination optical beams and to improve the resolution of the defect inspecting apparatus.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A defect inspecting apparatus comprising:

an illumination optical system configured to illuminate a mask having a patterned surface with an illumination optical beam;

an optical splitter configured to split the optical beam passing through the mask into two beam components, which is substantially arranged in an imaging plane on which the optical beam passing through the mask forms an image of the mask;

first and second image pickup sensors each having an array of pixels arranged on a longitudinal direction thereof and first and second pickup fields on the patterned surface, respectively, configured to pick up first and second parts of the mask image in the first and second pickup fields, the first and second pickup fields being parallel to each other and displaced from each other by (2n+1)×d/2 in the longitudinal direction thereof, where d denotes a longitudinal dimension of each pixel image in the first and second pick up fields and n denotes an integer equal to or larger than 0;

image merging part configured to merge the first and second parts of the mask image to form a pattern image, and a defect detector configured to detect a defect in the mask on the basis of the pattern image.

2. The defect inspecting apparatus according to claim 1, wherein the first and second pickup fields are displaced from each other by (2m+1)×d'/2 in a direction orthogonal to the longitudinal direction, where d' denotes the dimension of each pixel image in the first and second pickup fields along the orthogonal direction, and m denotes an integer equal to or larger than 0.

3. The defect inspecting apparatus according to claim 1, further comprising:

first and second imaging optical systems which guide the beam components to the first and second image pickup sensors, respectively, so that the first and second parts of the mask images are transferred to the first and second image pickup sensors, respectively; and position adjusting parts configured to adjusts a positional relationship between the first and second image pickup sensors in accordance with magnifications of the first and second imaging optical systems.

4. The defect inspecting apparatus according to claim 1, further comprising:

a moving table on which the mask is mounted, configured to move the mask along a direction orthogonal to the longitudinal direction in a first inspection and move the mask along the longitudinal direction to start a second inspection in which the mask is moved in the direction orthogonal to the longitudinal direction.

5. The defect inspecting apparatus according to claim 1, wherein the defect detector includes a comparator configured to compare the pattern image with the reference pattern image to detect the defect in the mask image.

6. A defect inspecting apparatus comprising:

an illumination optical system configured to illuminate a mask having a patterned surface with an illumination optical beam;

an optical splitter configured to split the optical beam directed from the mask into two beam components, which is substantially arranged in an imaging plane on which the optical beam passing through the mask forms an image of the mask;

first and second image pickup sensors each having an array of pixels arranged on a longitudinal direction thereof and first and second pickup fields on the patterned surface, respectively, configured to pick up first and second parts of the mask image in the first and second pickup fields, the first and second pickup fields being parallel to each other and displaced from one another by an odd-number multiple of half of a dimension of each pixel image in the first and second pick up fields;

first and second image transfer optical systems configured to transfer the first and second parts of the mask image to the first and second image pickup sensors, respectively;

image merging part configured to merge the first and second parts of the mask image to form a pattern image, and a defect detector configured to detect a defect in the mask on the basis of the pattern image.

7. The defect inspecting apparatus according to claim 6, wherein each of the first and second image transfer optical systems includes first and second magnification varying systems configured to vary magnification factor of the first and second image transfer optical systems, respectively, the first and second parts of the mask image being formed on the first and second image pickup sensors depending on the magnification factor; and first and second moving mechanisms configured to move the first and second image pickup sensors in such a manner that the first and second pickup fields are displaced from one another by about the odd-number multiple of half of the dimension of each pixel image in accordance with magnifications of the first and second magnification varying systems.

8. A defect inspecting apparatus comprising:

an illumination optical system configured to illuminate a mask having a patterned surface with an illumination optical beam;

first and second optical splitters configured to split the optical beam passing through the mask into three beam components, which is substantially arranged in an imaging plane on which the optical beam passing through the mask forms an image of the mask;

first, second and third image pickup sensors each having an array of pixels arranged on a longitudinal direction thereof and first, second and third pickup fields on the patterned surface, respectively, configured to pick up first, second and third parts of the mask image in the first, second and third pickup fields, the first, second and third pickup fields being parallel to each other, the first and second pickup fields being displaced from each other by (d/3+Nd) in the longitudinal direction thereof, and the second and third pickup fields being displaced from each other by (d/3Nd) in the longitudinal direction thereof, where d denotes a longitudinal dimension of each pixel image in the first, second and third pick up fields and N denotes an integer equal to or larger than 0;

image merging part configured to merge the first and second parts of the mask image to form a pattern image, and a defect detector configured to detect a defect in the mask on the basis of the pattern image.

9. The defect inspecting apparatus according to claim 8, further comprising:

first, second and third imaging optical systems which guide the beam components to the first, second and third image pickup sensors, respectively, so that the first, second and third parts of the mask images are transferred to the first, second and third image pickup sensors, respectively; and position adjusting parts configured to adjusts a positional relationship between the first, second and third image pickup sensors in accordance with magnifications of the first, second and third imaging optical systems.

10. The defect inspecting apparatus according to claim 8, further comprising:

a moving table on which the mask is mounted, configured to move the mask along a direction orthogonal to the longitudinal direction in a first inspection and move the mask along the longitudinal direction to start a second inspection in which the mask is moved in the direction orthogonal to the longitudinal direction.

11. The defect inspecting apparatus according to claim 8, wherein the defect detector includes a comparator configured to compare the pattern image with the reference pattern image to detect the defect in the mask image.

12. The defect inspecting apparatus according to claim 8, further comprising:

first, second and third imaging optical systems which guide the beam components to the first, second and third image pickup sensors, respectively, so that the first, second and third parts of the mask images are transferred to the first, second and third image pickup sensors, respectively, each of the first, second and third image transfer optical systems including first, second and third magnification varying systems configured to vary magnification factor of the first, second and third image transfer optical systems, respectively, the first, second and third parts of the mask image being formed on the first, second and third image pickup sensors depending on the magnification factor; and first and second moving mechanisms configured to move the first and second image pickup sensors in such a manner that the first and second pickup fields are displaced from one another by (d/3+Nd), and the first and third pickup fields are displaced from one another by (2d/3+Nd) in accordance with magnifications of the first, second and third magnification varying systems.

13. A method of inspecting a defect, comprising:

illuminating a mask having a patterned surface with an illumination optical beam;

splitting the optical beam passing through the mask into two beam components on an imaging plane on which an image of the mask is formed;

picking up first and second parts of the mask image in first and second pickup fields on the patterned surface by utilizing first and second image pickup sensors each having an array of pixels arranged on a longitudinal direction thereof, respectively, the first and second pickup fields being parallel to each other and displaced from each other by $(2n+1)\times d/2$ in the longitudinal direction thereof, where d denotes a longitudinal dimension of each pixel image in the first and second pick up fields and n denotes an integer equal to or larger than 0;

merging the first and second parts of the mask image to form a pattern image, and detecting a defect in the mask on the basis of the pattern image.

14. The defect inspecting method according to claim 13, wherein the first and second pickup fields are displaced from each other by $(2m+1)d'/2$ in a direction orthogonal to the longitudinal direction, where d' denotes the dimension of each pixel image in the first and second pickup fields along the orthogonal direction, and m denotes an integer equal to or larger than 0.

15. The defect inspecting method according to claim 13, further comprising:

guiding the beam components to the first and second image pickup sensors, respectively, so that the first and second parts of the mask images are transferred to the first and second image pickup sensors, respectively; and adjusting a positional relationship between the first and second image pickup sensors in accordance with magnifications of the mask image.

16. The defect inspecting method according to claim 13, further comprising:

moving the mask along a direction orthogonal to the longitudinal direction in a first inspection and moving the mask along the longitudinal direction to start a second inspection in which the mask is moved in the direction orthogonal to the longitudinal direction.

17. The defect inspecting method according to claim 13, wherein the defecting the defect includes comparing the pattern image with the reference pattern image to detect the defect in the mask image.

18. A method of inspecting a defect, comprising:

illuminating a mask having a patterned surface with an illumination optical beam;

splitting the optical beam directed from the mask into two beam components on an imaging plane on which an image of the mask is formed;

picking up first and second parts of the mask image in first and second pickup fields on the patterned surface by utilizing first and second image pickup sensors each having an array of pixels arranged on a longitudinal direction thereof, respectively, the first and second pickup fields being parallel to each other and displaced from one another by an odd-number multiple of half of a dimension of each pixel image in the first and second pick up fields;

transferring the first and second parts of the mask image to the first and second image pickup sensors, respectively;

merging the first and second parts of the mask image to form a pattern image, and detecting a defect in the mask on the basis of the pattern image.

19. The defect inspecting method according to claim 18, wherein the transferring the first and second parts includes varying magnification factor of the first and second image, respectively, the first and second parts of the mask image being formed on the first and second image pickup sensors depending on the magnification factor; and moving the first and second image pickup sensors in such a manner that the first and second pickup fields are displaced from one another by about the odd-number multiple of half of the dimension of each pixel image in accordance with the magnifications factors.

20. A method of inspecting a defect, comprising:

illuminating a mask having a patterned surface with an illumination optical beam;

splitting the optical beam passing through the mask into three beam components, which is substantially arranged in an imaging plane on which an image of the mask is formed;

picking up first, second and third parts of the mask image in first, second and third pickup fields on the patterned surface by utilizing first, second and third image pickup sensors each having an array of pixels arranged on a longitudinal direction thereof, respectively, the first, second and third pickup fields being parallel to each other, the first and second pickup fields being displaced from each other by (d/3+Nd) in the longitudinal direction thereof, and the second and third pickup fields being displaced from each other by (d/3+Nd) in the longitudinal direction thereof, where d denotes a longitudinal dimension of each pixel image in the first, second and third pick up fields and N denotes an integer equal to or larger than 0;

merging the first and second parts of the mask image to form a pattern image, and detecting a defect in the mask on the basis of the pattern image.

21. The defect inspecting method according to claim 20, further comprising:

guiding the beam components to the first, second and third image pickup sensors, respectively, so that the first, second and third parts of the mask images are transferred to the first, second and third image pickup sensors, respectively; and adjusting a positional relationship between the first, second and third image pickup sensors in accordance with magnifications of the first, second and third image.

22. The defect inspecting method according to claim 20, further comprising:

moving the mask along a direction orthogonal to the longitudinal direction in a first inspection and moving the mask along the longitudinal direction to start a second inspection in which the mask is moved in the direction orthogonal to the longitudinal direction.

23. The defect inspecting method according to claim 20, wherein the defecting the defect includes comparing the pattern image with the reference pattern image to detect the defect in the mask image.

24. The defect inspecting method according to claim 20, further comprising:

guiding the beam components to the first, second and third image pickup sensors, respectively, so that the first, second and third parts of the mask images are transferred to the first, second and third image pickup sensors, respectively, wherein each of the transferring the first, second and third image includes varying first, second and third magnification factor of the first, second and third image, respectively, the first, second and third parts of the mask image being formed on the first, second and third image pickup sensors depending on the magnification factor; and moving the first and second image pickup sensors in such a manner that the first and second pickup fields are displaced from one another by (d/3+Nd), and the first and third pickup fields are displaced from one another by (2d/3+Nd) in accordance with magnification factor.

* * * * *